United States Patent
Williamson

(10) Patent No.: US 12,156,698 B2
(45) Date of Patent: Dec. 3, 2024

(54) WIDE-ANGLE PUPIL RELAY FOR CELLPHONE-BASED FUNDUS CAMERA

(71) Applicant: NIKON CORPORATION, Tokyo (JP)

(72) Inventor: David M. Williamson, Tucson, AZ (US)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 18/143,916

(22) Filed: May 5, 2023

(65) Prior Publication Data
US 2023/0270328 A1    Aug. 31, 2023

Related U.S. Application Data

(63) Continuation of application No. 16/288,096, filed on Feb. 27, 2019, now Pat. No. 11,717,161, which is a
(Continued)

(51) Int. Cl.
*A61B 3/15* (2006.01)
*A61B 3/12* (2006.01)
(Continued)

(52) U.S. Cl.
CPC ............ *A61B 3/154* (2013.01); *A61B 3/12* (2013.01); *A61B 3/1208* (2013.01); *A61B 3/14* (2013.01); *A61B 3/152* (2013.01); *A61B 5/6898* (2013.01)

(58) Field of Classification Search
CPC ......... A61B 3/154; A61B 3/12; A61B 3/1208; A61B 3/14; A61B 3/152; A61B 5/6898; G02B 27/00
(Continued)

(56) References Cited

U.S. PATENT DOCUMENTS

| 4,423,932 A * | 1/1984 | Takahashi | A61B 3/14 351/207 |
| 4,502,766 A * | 3/1985 | Ito | A61B 3/14 396/18 |

(Continued)

FOREIGN PATENT DOCUMENTS

| CN | 204542052 U | 8/2015 |
| JP | S60-203233 A | 10/1985 |

(Continued)

OTHER PUBLICATIONS

English machine translation of the Office Action issued in corresponding Japanese Patent Application No. 2019-511667 dated Jun. 8, 2021 (4 pages).
(Continued)

*Primary Examiner* — Mohammed A Hasan
(74) *Attorney, Agent, or Firm* — FOLEY & LARDNER LLP

(57) ABSTRACT

An optical imaging system includes a first lens system housed in a body of a mobile telecommunication device, the first lens system having a first optical axis, a first entrance pupil fixed in space in a reference plane associated with said body, and a first focal length; and an optical telescope providing a diffraction-limited imaging within a spectral range from at least 486 nm to at least 656 nm. The optical imaging system is configured to image, when the optical telescope is inserted between the first lens system and an entrance pupil of a visual system of an eye (EPE), the EPE onto the first entrance pupil and vice versa with a substantially unit magnification.

9 Claims, 11 Drawing Sheets

Related U.S. Application Data continuation of application No. PCT/JP2017/031412, filed on Aug. 31, 2017.

(60) Provisional application No. 62/539,733, filed on Aug. 1, 2017, provisional application No. 62/381,768, filed on Aug. 31, 2016.

(51) Int. Cl.
  *A61B 3/14* (2006.01)
  *A61B 5/00* (2006.01)

(58) Field of Classification Search
  USPC .......................................................... 600/476
  See application file for complete search history.

(56) References Cited

U.S. PATENT DOCUMENTS

| | | | |
|---|---|---|---|
| 4,592,625 | A | 6/1986 | Uehara et al. |
| 5,061,054 | A | 10/1991 | Ohshita |
| 5,499,066 | A | 3/1996 | Farmer et al. |
| 6,550,917 | B1 | 4/2003 | Neal et al. |
| 7,287,854 | B2 | 10/2007 | Suzuki |
| 7,465,049 | B2 | 12/2008 | Maeda et al. |
| 7,830,525 | B2 | 11/2010 | Buckland et al. |
| 10,835,119 | B2 * | 11/2020 | Izatt .................... A61B 3/1208 |
| 11,717,161 | B2 * | 8/2023 | Williamson ........... A61B 3/154 600/476 |
| 2001/0041884 | A1 | 11/2001 | Frey et al. |
| 2003/0206272 | A1 * | 11/2003 | Cornsweet ............. A61B 3/156 351/206 |
| 2006/0077346 | A1 * | 4/2006 | Matsumoto .............. A61B 3/12 351/205 |
| 2007/0002276 | A1 | 1/2007 | Hirohara et al. |
| 2011/0080562 | A1 | 4/2011 | Iizuka et al. |
| 2011/0286025 | A1 * | 11/2011 | Silverbrook ......... H04N 1/4433 358/1.14 |
| 2012/0050673 | A1 | 3/2012 | Shikaumi |
| 2012/0320340 | A1 | 12/2012 | Coleman, III |
| 2013/0100407 | A1 | 4/2013 | Iwanaga et al. |
| 2015/0045012 | A1 | 2/2015 | Siminou |
| 2015/0103317 | A1 | 4/2015 | Goldfain et al. |
| 2015/0146196 | A1 | 5/2015 | Huang |
| 2015/0245765 | A1 * | 9/2015 | Fujii ...................... A61B 3/102 351/206 |
| 2018/0116502 | A1 | 5/2018 | Ishinabe |

FOREIGN PATENT DOCUMENTS

| | | |
|---|---|---|
| JP | 2000-107134 | 4/2000 |
| JP | 2002-150274 | 5/2002 |
| JP | 2003-019118 A | 1/2003 |
| JP | 2003-202626 | 7/2003 |
| JP | 2006-314650 A | 11/2006 |
| JP | 4094378 B2 | 6/2008 |
| JP | 2008-197190 A | 8/2008 |
| JP | 2013-255859 A | 12/2013 |
| JP | 3197418 U | 5/2015 |
| WO | WO-2015/054672 | 4/2015 |
| WO | WO-2015/071779 A1 | 5/2015 |
| WO | WO-2015/107373 A1 | 7/2015 |
| WO | WO-2016/127140 A1 | 8/2016 |

OTHER PUBLICATIONS

English translation only of Office Action issued in corresponding Japanese Patent Application No. 2019-511667 dated Feb. 16, 2021.
Extended European Search Report (EESR) issued in corresponding European Patent Application No. 17846661.1 dated Mar. 27, 2020.
Foreign Action other than Search Report on non-Foley case related to U.S. Appl. No. 16/288,096 DTD Feb. 16, 2021.
International Search Report and Written Opinion issued in International Application No. PCT/JP2017/031412 dated Oct. 31, 2017 (12 pages).
Japanese Office Action issued in corresponding Japanese Patent Application No. 2019-511667, dated Aug. 9, 2022 with Machine translation (37 pages).
JP Office Action issued in corresponding Japanese Patent Application No. 2019-511667 dated Sep. 7, 2021 with English translation (10 pages).
JP Office Action issued in corresponding Japanese Patent Application No. 2021-198874, dated Nov. 8, 2022 (9 pages).
Samaneigo et al.,Rice University, mobileVision Final Report dated Spring 2012 (96 pages).
US Non-Final Office Action on U.S. Appl. No. 16/288,096 dated Aug. 17, 2022 (10 pages).
US Notice of Allowance on U.S. Appl. No. 16/288,096 dated Feb. 7, 2023 (8 pages).
Office Action issued in corresponding Japanese Patent Application No. 2021-198874, dated Jun. 13, 2023 (9 pages).
Japanese Office Action issued in corresponding Japanese Patent Application No. 2023-148826, dated Jul. 2, 2024 (8 pages).

* cited by examiner

[Fig. 6A]
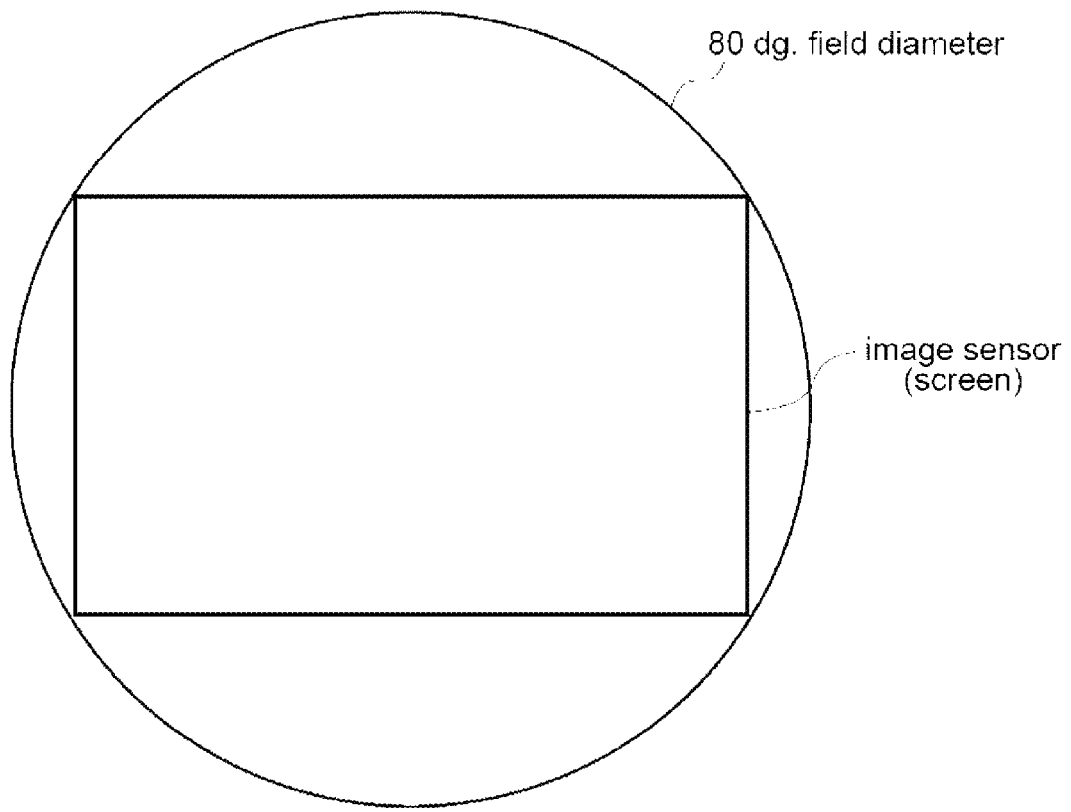
[Fig. 6B]
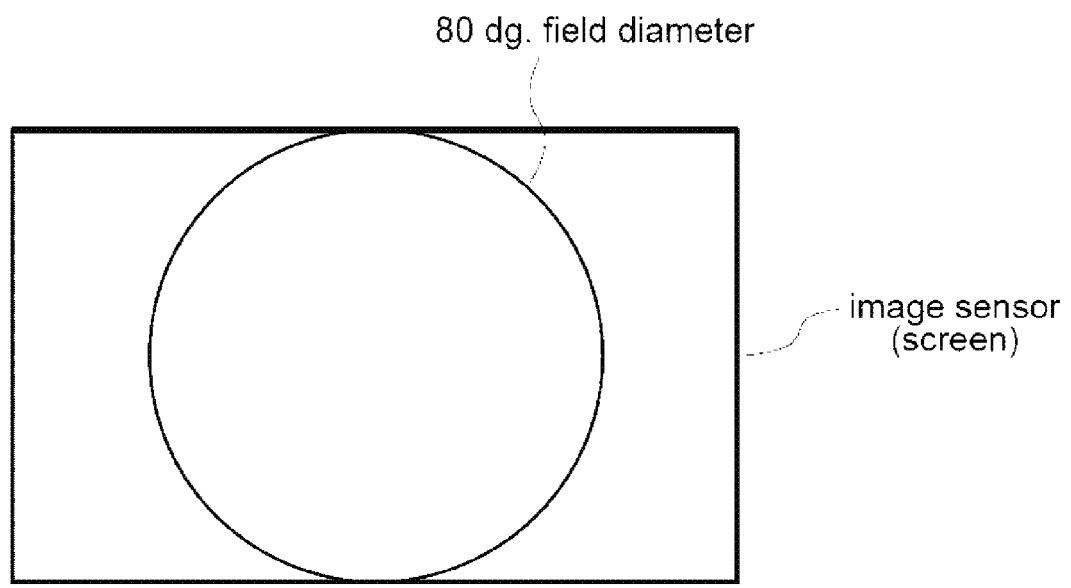

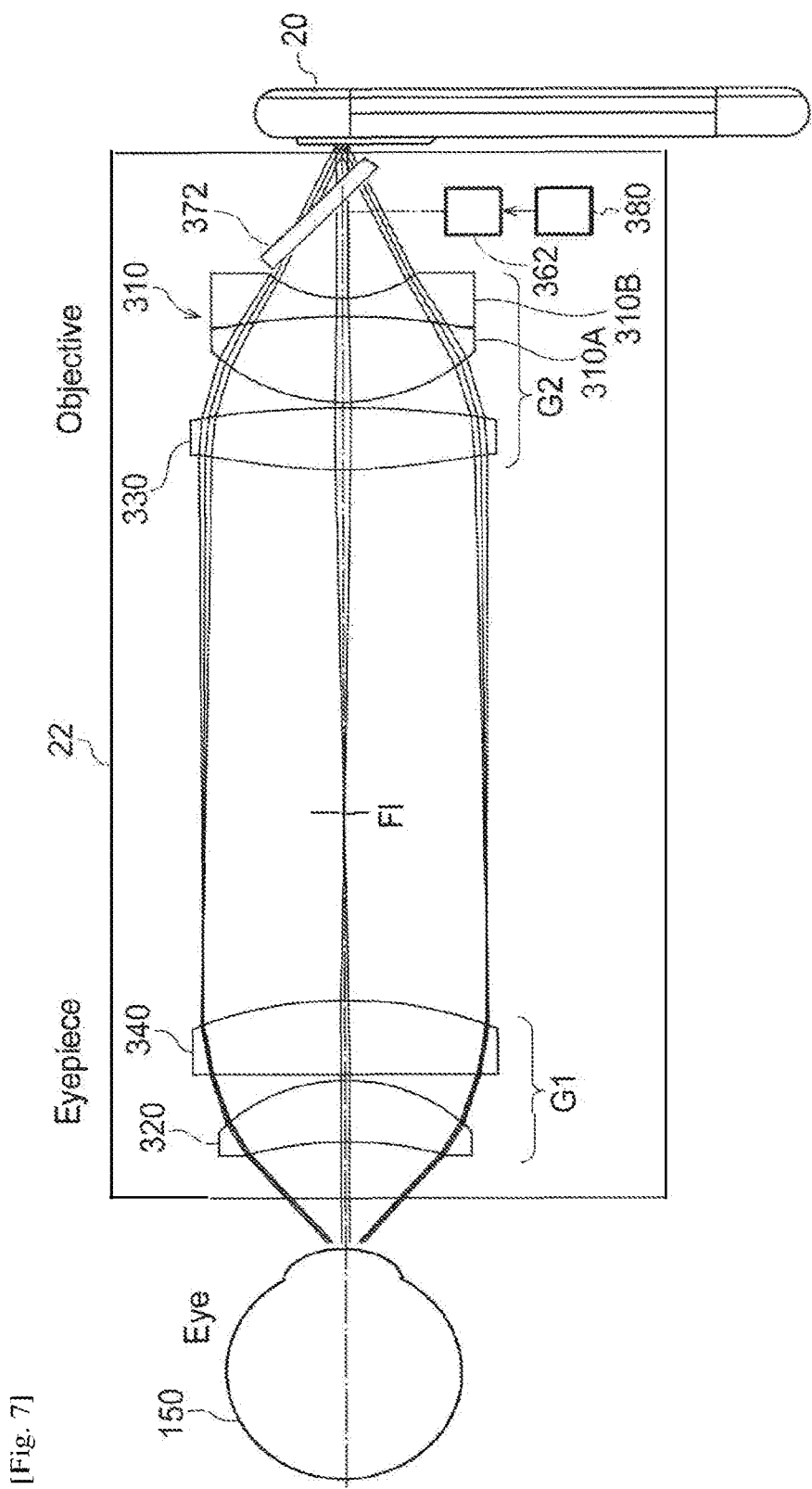
[Fig. 7]

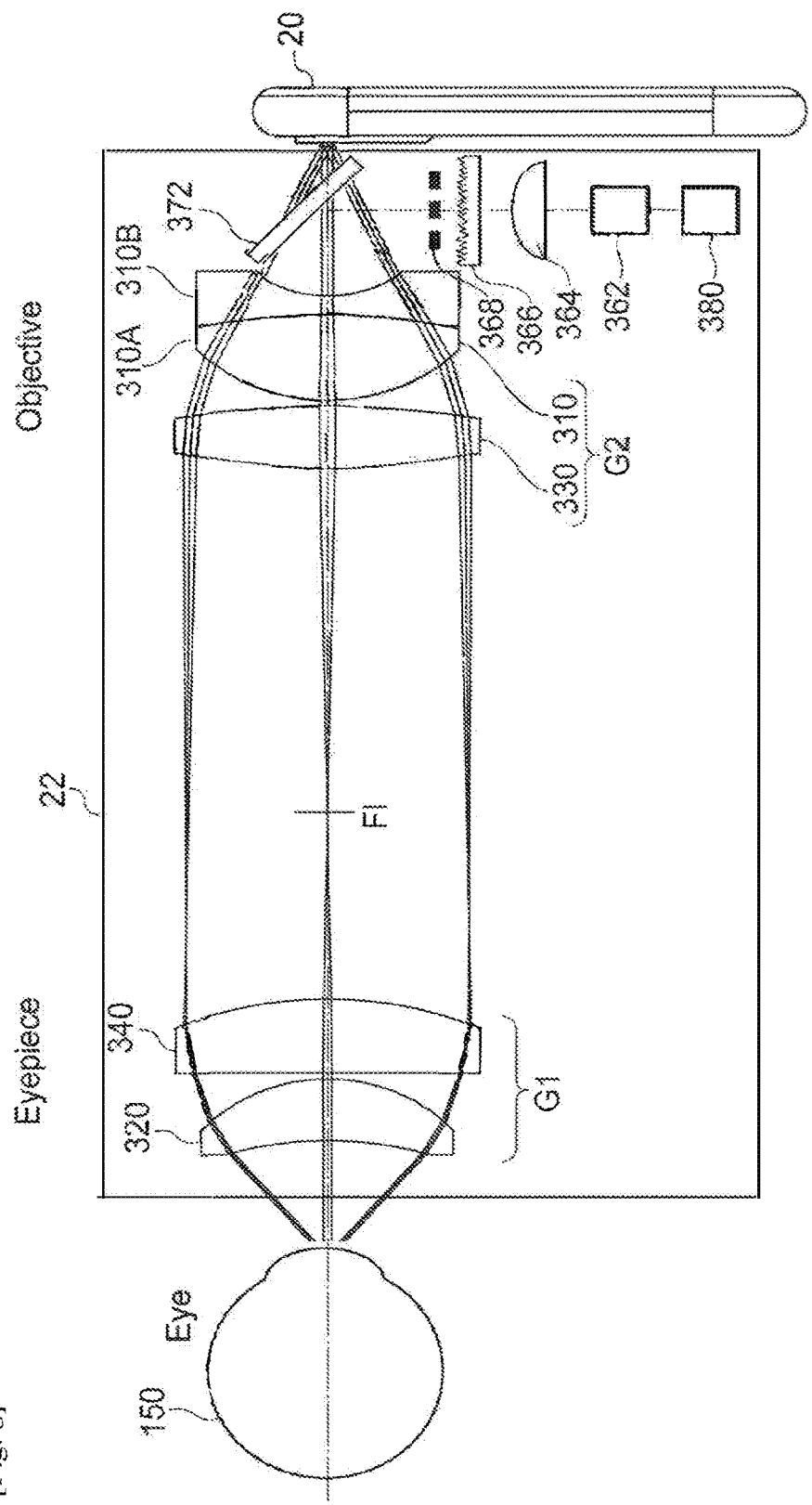
[Fig. 8]

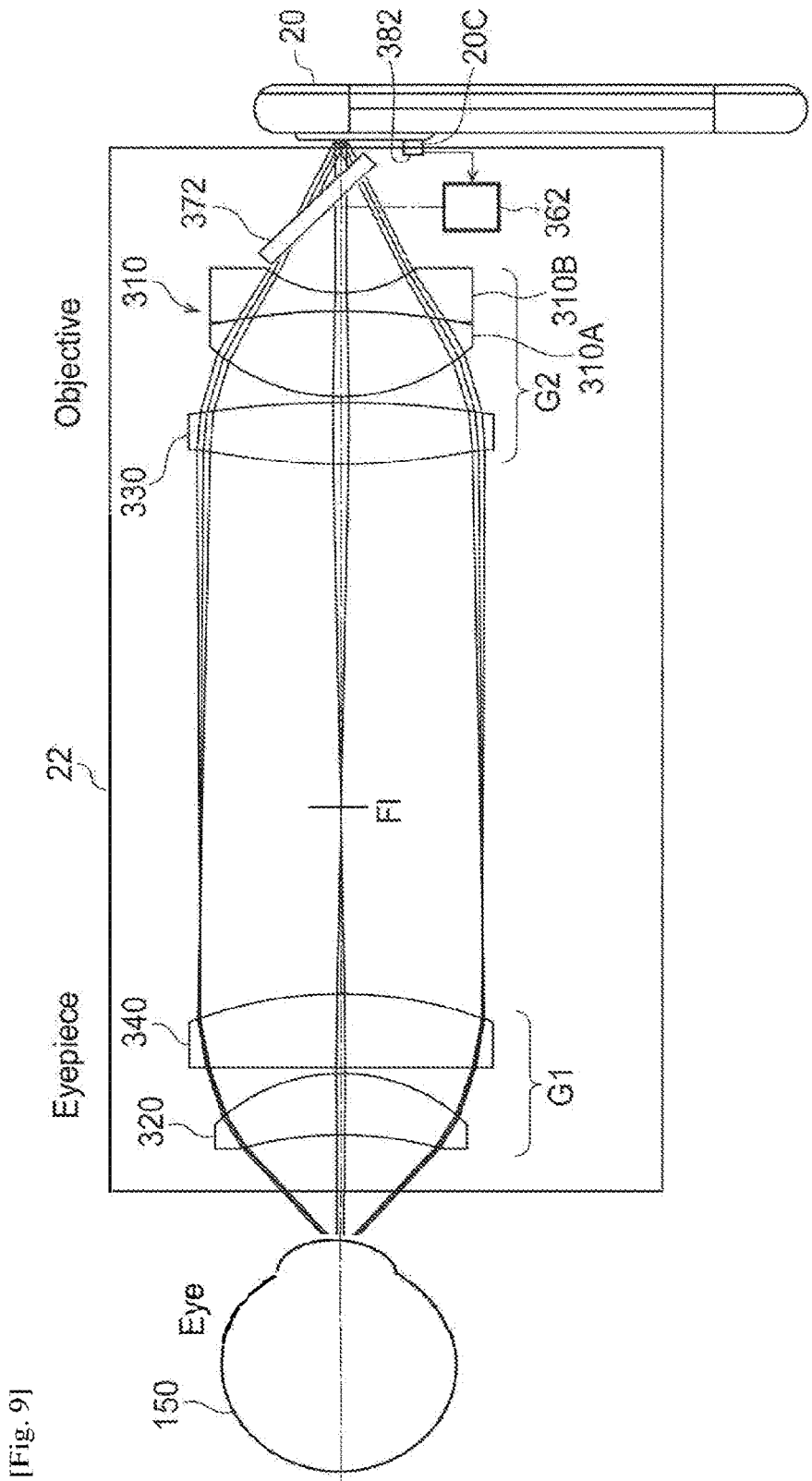
[Fig. 9]

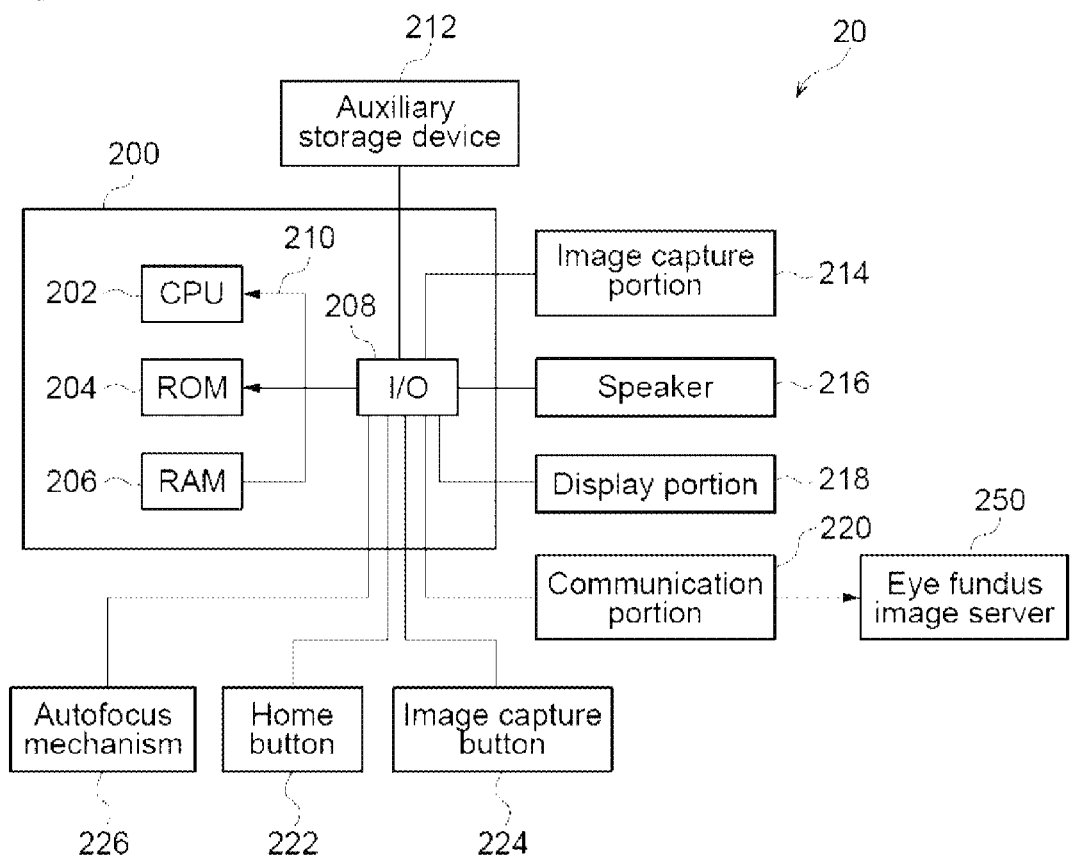
[Fig. 10]

[Fig. 11]
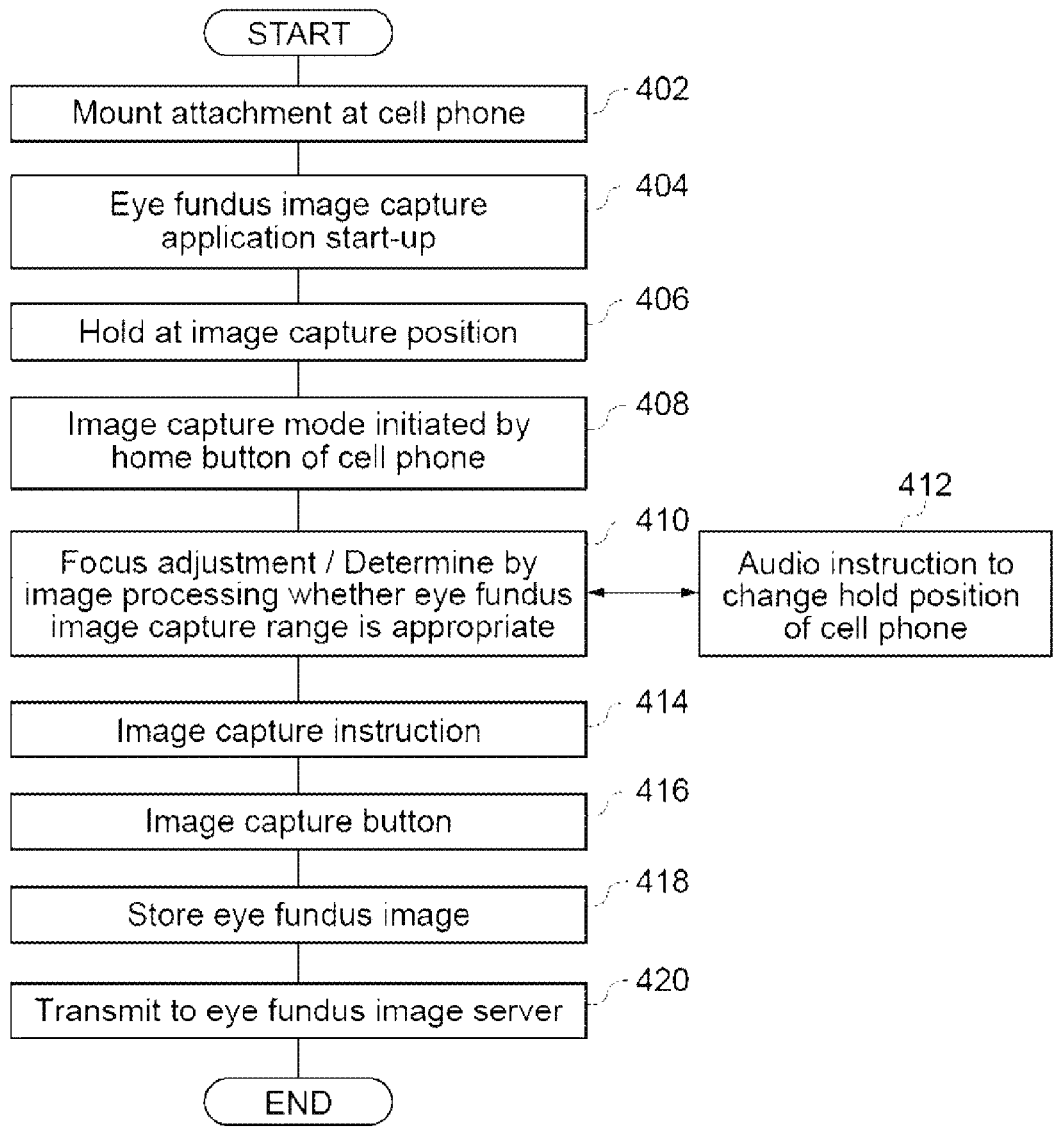

WIDE-ANGLE PUPIL RELAY FOR CELLPHONE-BASED FUNDUS CAMERA

The present invention is a Continuation of U.S. patent application Ser. No. 16/288,096, filed Feb. 27, 2019, which is a Continuation of PCT International Application No. PCT/JP2017/031412, filed Aug. 31, 2017, which claims priority to US Provisional Patent Application Nos. 62/381,768 filed on Aug. 31, 2016, and 62/539,733 filed on Aug. 1, 2017. The disclosures of these applications are incorporated herein by reference.

TECHNICAL FIELD

The present invention relates generally to ocular diagnostic imaging devices, and more particularly, to a portable handheld smart phone-based retinal camera, configured to capture high-quality, wide field fundus images. The use of the mobile phone platform creates a fully embedded system capable of acquisition, storage, and analysis of fundus images that can be directly transmitted from the phone via the wireless telecommunication system for remote evaluation.

BACKGROUND ART

Fundus imaging is used extensively in the diagnosis, monitoring, and management of many retinal diseases. One limitation found in current imaging systems is the bulky and stationary nature of the imaging equipment. Conventional fundus cameras are cumbersome tabletop devices that are not readily mobile due to the fragility, large size and heavy weight of these devices. In practice, such fundus cameras also force the patient to be seated upright, which can be difficult for sick and hospitalized patients. In addition to dimensional constraints, fundus cameras require a power source to supply power to the illumination, imaging screen, and data processing unit. Often this power source is provided by central in-wall power plugs, and continuous electrical power is required in order for the fundus camera to function properly.

While digital fundus cameras have been envisioned (some of these on the basis of a cellphone or similar devices such as an iPhone; generally, a mobile device), such cameras possess substantial operational limitations caused by any of (i) a lack of optical conjugation between the optical system of the used mobile device and the vision system being imaged; (ii) an insufficient field-of-view (FOV) associated with imaging of the chosen surface of the vision system, which results in a need for multiple computational "stitching" of the acquired images; (iii) severe residual aberrations impairing the resulting images, and (iv) combinations of the above.

Accordingly, there remains a need for a low-cost handheld device configured to function as a substitute for high-cost medical devices and enable the recording of digital images of the surface(s) of a vision system during an ophthalmic examination thereof, while being devoid of the operational shortcomings characterizing currently known imaging system solutions.

SUMMARY OF INVENTION

A first aspect of the present disclosure includes: a first lens system housed in a body of a mobile telecommunication device, the first lens system having a first optical axis, a first entrance pupil fixed in space in a reference plane associated with the body, and a first focal length; and an optical telescope providing diffraction-limited imaging within a spectral range from at least 486 nm to at least 656 nm wherein the optical system is configured to image, when the optical telescope is inserted between the first lens system and an entrance pupil of a visual system of an eye (EPE), the EPE onto the first entrance pupil and vice versa with a substantially unit magnification.

BRIEF DESCRIPTION OF DRAWINGS

The invention will be more fully understood by referring to the following Detailed Description of Specific Embodiments in conjunction with the not-to scale Drawings.

FIG. 6A is a diagram showing a size relationship between an image capture field-of-view of the eye fundus and an image sensor in the first embodiment.

FIG. 6B is a diagram showing a size relationship between an image capture field-of-view of the eye fundus and an image sensor in the second embodiment.

FIG. 7 is a schematic diagram illustrating the configuration of attachment 22 according to a third embodiment.

FIG. 8 is a schematic diagram illustrating the configuration of attachment 22 according to a fourth embodiment.

FIG. 9 is a schematic diagram illustrating the configuration of attachment 22 according to a fifth embodiment.

FIG. 10 is a diagram illustrating the electrical configuration of cellphone 20.

FIG. 11 is a flowchart explaining a method of use of attachment 22 and cellphone 20.

Generally, the sizes and relative scales of elements in Drawings may be set to be different from actual ones to appropriately facilitate simplicity, clarity, and understanding of the Drawings. For the same reason, not all elements present in one Drawing are necessarily shown in another.

DESCRIPTION OF EMBODIMENTS

Figure 1:
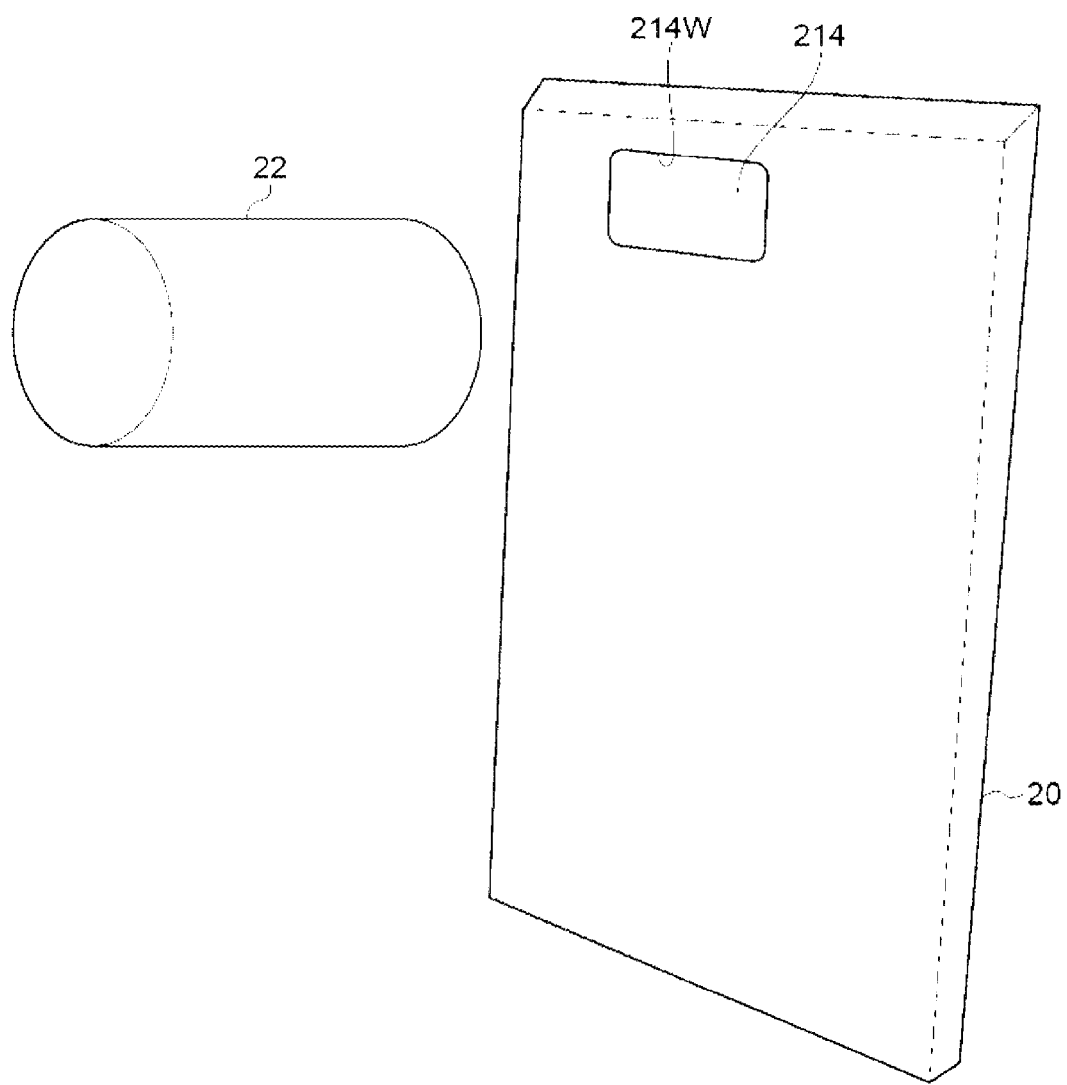
FIG. 1 is a diagram that shows cellphone 20, which is provided with image capture portion (camera sensor) 214 that captures an image of the eye fundus of a subject eye via window 214W and via an optical system that is not shown (image capture lens system (camera lens)), and shows attachment 22, which is attached to cellphone 20.

FIG. 1 shows cellphone 20, which is provided with image capture portion (camera sensor) 214 that captures an image of the eye fundus of a subject eye via window 214W and via an optical system that is not shown (image capture lens system (camera lens)), and shows attachment 22, which is attached to cellphone 20.

In the explanation of the present invention, a cellphone is identical to a device referred to as a mobile telecommunication device, a mobile phone, or a wireless telecommunication system, and a fundus camera is identical to a device referred to as a portable handheld smart phone-based retinal camera or a low-cost handheld device.

The cellphone camera lens is the imaging lens on the camera sensor. Of course, these are already provided by cellphone manufacturers.

The present inventor makes use of extremely useful properties of the cellphone camera lens; namely, the lens is approximately diffraction-limited, and the entrance pupil is at the front of the lens, just inside the window of the cellphone camera.

If a cellphone has both wide angle and telephoto cameras, these both have their entrance pupils substantially in the same location. This means that if the cellphone is mechanically-shifted laterally, either cellphone camera can be used. Thus, simple zooming is possible without a large loss of pixels between a 40 dg and 80 dg field-of-view fundus camera.

Another useful feature of cellphone camera lenses is that the fields of view are similar to what is desired for a fundus camera, so the pupil relay can be close to 1× magnification, which means that lateral chromatic aberration and distortion can be small, and the optical design relatively simple.

The coarse focus is a mechanical adjustment of the separation between the lens group G1 and the second lens group G2 to accommodate different patients' Diopter settings. The fine focus is the cellphone camera's built-in autofocus system.

In accordance with disclosed embodiments of the present invention, a modular apparatus and method for use of the same are disclosed for a handheld, ocular imaging device complemented with an imaging optical detection system (a camera), and a programmable processor of a mobile phone, (alternatively, a tablet or another smart device) operably coupled to optical elements and illumination elements, configured to image the structure(s) of the eye (such as a retina) in a non-clinical location. The modular apparatus provides multi-functionality (fluorescein imaging, fluorescence, bright field, infrared (IR) imaging, near-infrared (NIR) imaging) and multi-region imaging (retinal, corneal, external, etc.) of the eye along with the added features of image processing, storage and wireless data transmission for remote storage and evaluation. Acquired ocular images can also be transmitted directly from the device to the electronic medical records of a patient without the need for an intermediate computer system.

The field of view (FOV) of the retina is a technical specification of fundus imaging that is an important consideration in fundus camera development. The FOV describes the angle through the pupil of an eye at which the retina is imaged. The illuminating light from the device enters the retina and the reflected light from the retina is used to form an image at the sensor of the device. A standard fundus camera has an approximately 40-45 degree FOV.

In a digital imaging system disclosed at <peekvision.org/what-it-does> (referred to herein as a Peek system), for example, a cellphone camera is used to take a picture of the user's retina by being placed as close as possible to the user's eye. In this situation, the entrance pupil (EP) of the cellphone optical system (which is typically located at the front lens element just inside its front window) is not optically-conjugate with the user's eye EP or iris (that is, with the EP of the vision system being inspected). (A device that is similarly limited in configuration and operation is disclosed at <www.d-eyecare.com>.) As a result—as would be readily appreciated by a skilled artisan—the image of the retina formed by the employed optical system inevitably contains significant aberrations that, under normal uncorrected/unattended-to circumstances, do not allow the user to correctly assess the conditions/status of the imaged retina as intended. In particular, the FOV associated with the imaging of the retina with the Peek system is, therefore, limited substantially by the ratio of the eye-pupil diameter to the dimension of the foveal region around the optic nerve and macular region, and the image quality is poor. While this solution provides useful low-cost diagnostic information for some retinal pathologies, it would be advantageous to image a larger area of the retina, at higher resolution, such that other more subtle retinal pathologies may be observed.

A fundus camera of Bosch, described at <bosch-eyecare.com/en/eyecare/products/fundus_imaging/fundus_imaging.html>, is also limited to imaging within a +/−40 degree FOV; Jedmed describes a similar system: <jedmed.com/products/portable-fundus-camera>. A solution provided by Volk Optical is another example (see <veatchinstruments.com/Volk-Pictor-Plus-Portable-Retinal-Camera>) of an operationally-limited system in terms of imaging the retinal surface.

The operational problems associated with existing fundus cameras of the related art (possessing low FOV, which results in the need for multiple computational "stitching" of optical data acquired from a retina, and substantial residual aberrations, causing detrimental reduction in the overall quality of the resulting "stitched" image) are solved by providing a compact, low cost Fundus camera with a wide 80 degree (full angle) FOV configured as an achromatic afocal relay (telescope) operating at a magnification level close to 1× to effectuate imaging of a 2 mm diameter (undilated) eye pupil into the spatially-fixed EP of the optical system of the mobile device with a diffraction-limited resolution.

Embodiments of the present invention take advantage of the parameters of a typical, built-in imaging optical system of a cellphone (or another mobile device), which possesses a full-angle FOV of about 75 to 80 degrees and is assumed to have no aberrations or vignetting (which is a reasonable assumption considering the nominal diffraction-limited performance of such optical systems as known in the art) and an EP size of about 2 mm in diameter (the EP of the mobile device being fixed in space), to provide an approximately 1× optical relay system for imaging the EP of the eye to the EP of the mobile device.

Considering the dimensional match, typically available between the EP of the undiluted eye and that of the optical system of the typical mobile device, the afocal relay of the invention is structured to provide imaging with approximately 1× magnification, thereby ensuring a full-angle FOV at the entrance of the eye of about 80 degrees. This is about twice that of a typical Fundus camera of the related art and about half the full horizontal field of view of the human eye. Therefore, a single imaging exposure with the use of the lens of the invention covers a substantially larger area of the retina than a typical fundus camera. Moreover, in the case that spatial stitching of several (for example, four) shots of images of the retina procured with the lens system of the invention is attempted, not only would the "stitched" image cover the whole retina, but the stitching would be available while maintaining an almost 50% overlap between stitched individual fields. A person of skill in the art will readily appreciate that such spatial overlap of constituent individual images is not possible with the use of a system described in the related art. Because existing systems have a much smaller field of view, 40 degrees or less, one has to overlap many more individual images (acquired with an existing system) to cover the whole retina (about 160 degrees), or, alternatively, to have a smaller overlap. However, it is recognized in the art that the larger the overlap between or among the constituent images, the better the quality of the resulting stitched image, because there are more features (mostly blood vessels in case of imaging the retina) to use for alignment. The advantage of the present embodiment is that each individual constituent image covers more of the retinal surface, so that one can afford to increase the area of the overlap between the constituent images when forming the resulting stitched image.

Figure 2:
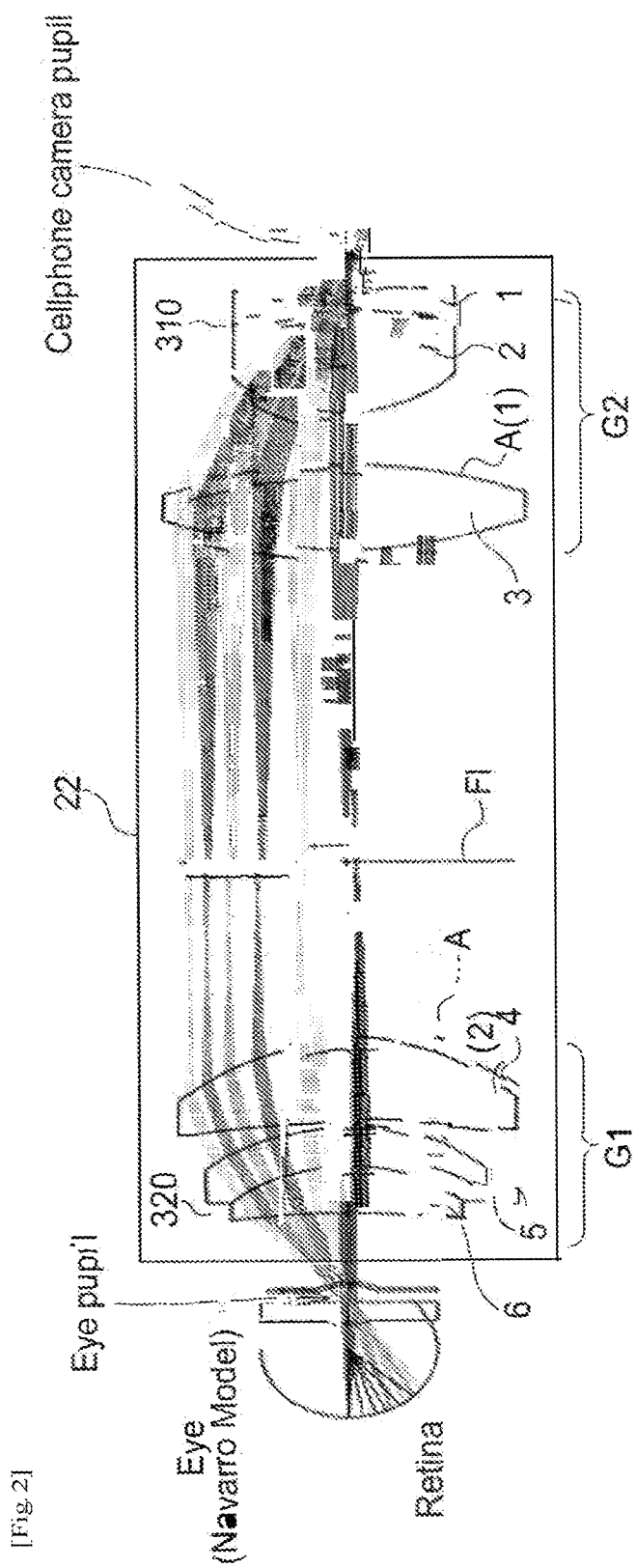
FIG. 2 is a schematic diagram of the optical train of the first embodiment complementing the exit pupil of the portable device and relaying the image of the cellphone camera pupil onto the eye pupil.

FIG. 2 shows a Y-Z cross section through an implementation of a lens system of the first embodiment-here, configured as a rotationally-symmetrical dioptric afocal relay (telescope). For convenience, as shown, rays are traced from the cellphone camera EP on the right of FIG. 2 through the optical system in attachment 22, to a Navarro model eye on the left of FIG. 2. The lens element closest to the cellphone camera pupil is labeled as element 1 in FIG. 2; the next lens element is element 2, and so on, while the retinal surface is referred to as an image plane. The design includes two cemented doublets (320 by the EP of the eye and 310 by the EP of the cellphone camera lens), while the single positive biconvex lens 3 has the highest converging power among the optical elements present in the embodiment. The cemented doublet lens 320 is composed of a positive meniscus lens element 6 concave to the eye side cemented with a meniscus lens element concave to the eye side. The first lens group G1 includes the cemented doublet lens 320 and a positive meniscus lens element 4 concave to the eye side. The cemented doublet lens 310 is composed of a biconcave negative lens element 1 cemented with a biconvex positive lens element 2. The second lens group G2 includes the cemented doublet lens 310 and a positive biconvex lens element 3.

Figure 3:
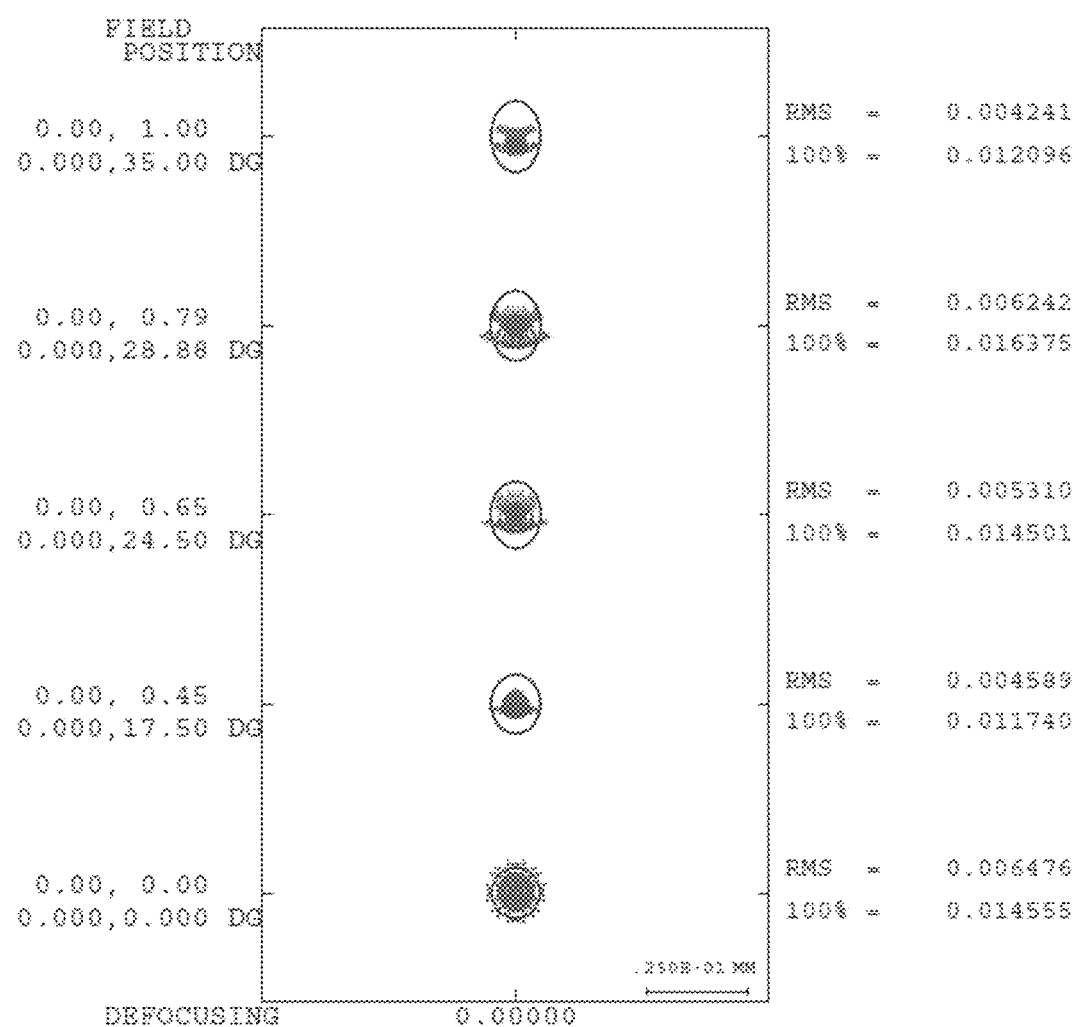
FIG. 3 includes spot diagrams characterizing diffraction-limited quality of imaging with the first embodiment of FIG. 2 for different field heights.

Working close to 1× magnification is desirable and provides clear operational advantages over the systems of the related art, as such optical configuration facilitates the correction of lateral color and distortion aberrations, in stark contradistinction with the systems of the related art. The optical design of FIG. 2 is configured to compensate for the aberrations of the (Navarro model) eye (at 2 mm eye pupil diameter, the healthy human eye is almost diffraction-limited) and provides close to diffraction-limited resolution across the entire 80 degree FOV. The evidence of this operational characteristic is provided in FIG. 3, which shows ray aberrations (spot diagrams) in the planes that are locally tangential to the spherical retina, at three identified wavelengths, 643.85 nm, 546.1 nm, and 479.99 nm. As shown in FIG. 3 and convincingly evidenced by the spot diagrams falling within the Airy disk curve for each of the wavelengths, aberrations are substantially corrected over the whole visible spectrum, but are even smaller at the red end of the spectrum (where the backscattered light from the retina is about five times stronger than that in the blue, which is operationally preferred during the imaging of the retina). Such diffraction-limited performance across the visible spectrum critically and advantageously distinguishes the proposed invention from that of the related art. In practice, the proposed design of the optical system is such that diffraction-limited imaging of the retina is effectuated by balancing of optical aberrations typical for an average eye with those of the eye piece portion of the embodiment of the invention.

Several notes are in order concerning an objective utilized in an embodiment of the system of the invention. Tables 1, 2, and 3 provide data representing an optical train (sequence) of lens elements of the first embodiment of FIG. 2, and Table 4, 5 and 6 provide data representing an optical train (sequence) of lens elements of the second embodiment of FIG. 4, forming lens systems configured according to the idea of the invention. The design prescriptions for the embodiments were generated with Code V and are discussed in reference to the corresponding Drawings. In these Tables, optical elements and, possibly, media separating some of the elements, are numbered in a "backward" fashion, starting from that which is the closest to the object/target plane (illustrated in FIG. 4) towards the retinal surface of an eye. This approach to the numbering of the optical elements makes it easier, as would be appreciated by a skilled artisan, to define the NA and parameters characterizing the behavior of the system in the image space—that is, in the space of the eye—during the process of optical design. The closest lens element to the object is labeled as element 1 both in Table 4 and FIG. 4; the next lens element is element 2, and so on, while the retinal surface is referred to as an image plane. Notably, the combination with the Navarro model of the human eye is chosen, the typical optical properties and geometrical characteristics of which have to be included in the design of the relay system of the invention for proper assessment of the system.

Positive radius value for a Liven surface indicates that the center of curvature of this surface is to the left of the surface, while a negative radius value indicates that the center of curvature is to the right of the surface; dimensions are provided in millimeters; thickness is defined as an axial distance from a given surface to the next surface; and an indicated image diameter is a paraxial value and not a ray-traced value. Additionally, with respect to the description of chromatic aberrations—if present—a reduction in Strehl ratio between monochromatic and polychromatic designs represents the contrast loss from chromatic aberrations over the specified spectral band, while a variation in best individual focus shows the residual field curvature.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor, mean "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. When used in reference to a numerical value, the terms represent a range of plus or minus 20% with respect to the specified value, more preferably plus or minus 10%, even more preferably plus or minus 5%, and most preferably plus or minus 2% with respect to the specified value.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes. In some specific cases, which are within the scope of the invention, the terms "approximately" and "about", when used in reference to a numerical value, represent a range of plus or minus 20% with respect to the specified value, more preferably plus or minus 10%, even more preferably plus or minus 5%, and most preferably plus or minus 2% with respect to the specified value.

TABLE 1

(Embodiment 1)

| ELEMENT NUMBER | RADIUS OF CURVATURE FRONT | RADIUS OF CURVATURE BACK | THICKNESS | APERTURE DIAMETER FRONT | APERTURE DIAMETER BACK | nd | Vd |
|---|---|---|---|---|---|---|---|
| OBJECT | ∞ | | INFINITY | 2.0000 | | | |
| APERTURE STOP | | | 6.3116 | | | | |
| 1 | −14.2165 CC | 51.3347 CC | 2.9966 | 9.6557 | 14.2680 | 1.846 | 23.8 |
| 2 | 51.3347 CX | −19.9198 CX | 18.0063 | 14.2680 | 28.6892 | 1.677 | 55.1 |
| | | | 9.1964 | | | | |
| 3 | 61.3624 CX | A(1) | 15.0162 | 44.9001 | 46.1126 | 1.517 | 64.2 |
| | | | 54.8338 | 43.1273 | | | |
| | | | 30.8400 | | | | |
| 4 | A(2) | 111.1392 CC | 14.4372 | 43.2966 | 39.5928 | 1.517 | 64.2 |
| | | | 1.0000 | | | | |
| 5 | 27.7511 CX | 22.3289 CC | 7.2581 | 35.9187 | 29.2285 | 1.922 | 20.8 |
| 6 | 22.3289 CX | 100.0000 CC | 8.2817 | 29.2285 | 25.5733 | 1.640 | 60.1 |
| | | | 10.0000 | 10.1554 | | | |
| 7 | Navarro eye model | | 2.0900 | | | | |

NOTES
Positive radius indicates the center of curvature is to the right
Negative radius indicates the center of curvature is to the left
Dimensions are given in millimeters
Thickness is axial distance to next surface
The Navarro eye model is described in J Opt Soc Am A. 1985 August; 2(8): 1273-81.
Accommodation-dependent model of the human eye with asperics.
Navarro R, Santamaria J. Bescos J.

TABLE 2

ASPHERIC CONSTANTS
$$Z = ((CURV)*Y^2)/(1 + [1 - (1 + K)*(CURV)^2 Y^2]^{1/2}) + (A)*Y^4 + (B)*Y^6 + (C)*Y^8 + (D)*Y^{10}$$

| ASPHERIC | CURV | K | A | B | C | D |
|---|---|---|---|---|---|---|
| A(1) | −0.02129068 | −4.40856200 | −2.07205E−07 | 6.94266E−10 | −9.25536E−14 | 0.00000E+00 |
| A(2) | 0.03723186 | −0.99124670 | 3.54873E−06 | −1.20826E−09 | −1.41664E−12 | 0.00000E+00 |

REFERENCE WAVELENGTH = 587.6 NM
SPECTRAL REGION = 486.1-656.3 NM

TABLE 3

INFINITE CONJUGATES

| | |
|---|---|
| EFL = | −22.2382 |
| BFL = | 12.1279 |
| FFL = | −18.1278 |
| F/NO = | −8.3228 |
| IMAGE DIST = | 12.0500 |
| OAL = | 192.1880 |
| PARAXIAL IMAGE HT = | 11.6554 |
| SEMI-FIELD ANGLE = | 35.0000 |
| ENTR PUPIL DIAMETER = | 2.0000 |
| DISTANCE = | 0.0000 |
| EXIT PUPIL DIAMETER = | 1.8365 |
| DISTANCE = | −8.2919 |

NOTES
FFL is measured from the first surface
BFL is measured from the last surface

TABLE 4

(Embodiment 2)

| ELEMENT NUMBER | RADIUS OF CURVATURE FRONT | RADIUS OF CURVATURE BACK | THICKNESS | APERTURE DIAMETER FRONT | APERTURE DIAMETER BACK | nd | Vd |
|---|---|---|---|---|---|---|---|
| OBJECT | ∞ | | INFINITY | 2.0000 | | | |
| APERTURE STOP | | | 30.0000 | | | | |
| 1 | −20.8494 CC | 102.4570 CC | 3.5877 | 25.6282 | 36.8675 | 1.688 | 31.2 |
| 2 | 102.4570 CX | −32.3754 CX | 16.7148 | 36.8675 | 43.7003 | 1.788 | 47.3 |
| | | | 1.1911 | | | | |
| 3 | 158.0684 CX | A(1) | 12.0000 | 49.9597 | 50.9992 | 1.788 | 47.3 |
| | | | 66.6381 | 50.3388 | | | |
| | | | 37.0080 | | | | |

TABLE 4-continued (Embodiment 2)

| ELEMENT NUMBER | RADIUS OF CURVATURE | | THICKNESS | APERTURE DIAMETER | | nd | Vd |
|---|---|---|---|---|---|---|---|
| | FRONT | BACK | | FRONT | BACK | | |
| 4 | 68.0998 CX | INF | 14.4000 | 50.8799 | 47.7850 | 1.788 | 47.3 |
| | | | 1.2000 | | | | |
| 5 | 29.7274 CX | 60.2508 CC | 12.0000 | 41.8696 | 35.0824 | 1.788 | 47.3 |
| | | | 18.0000 | 9.3366 | | | |
| 6 | Navarro eye model | | 2.0900 | | | | |

NOTES
Positive radius indicates the center of curvature is to the right
Negative radius indicates the center of curvature is to the left
Dimensions are given in millimeters
Thickness is axial distance to next surface
The Navarro eye model is described in J Opt Soc Am A. 1985 August; 2(8): 1273-81.
Accommodation-dependent model of the human eye with aspherics.
Navarro R. Santamaria. J. Bescos J.

TABLE 5

ASPHERIC CONSTANTS
$Z = ((CURV)*Y^2)/(1 + [1 - (1 + K)*(CURV)^2 Y^2]^{1/2}) + (A)*Y^4 + (B)*Y^6 + (C)*Y^8 + (D)*Y^{10}$

| ASPHERIC | CURV | K | A | B | C | D |
|---|---|---|---|---|---|---|
| A(1) | −0.01070741 | −1.00000000 | 1.41214E−06 | −2.35725E−11 | 1.98134E−13 | 0.00000E+00 |

REFERENCE WAVELENGTH = 587.6 NM
SPECTRAL REGION = 486.1-656.3 NM

TABLE 6

| INFINITE CONJUGATES | |
|---|---|
| EFL = | −30.6757 |
| BFL = | 12.0923 |
| FFL = | −34.3970 |
| F/NO = | −11.4806 |
| IMAGE DIST = | 12.0500 |
| OAL = | 226.7496 |
| PARAXIAL IMAGE HT = | 10.5974 |
| SEMI-FIELD ANGLE = | 24.7750 |
| ENTR PUPIL DIAMETER = | 2.0000 |
| DISTANCE = | 0.0000 |
| EXIT PUPIL DIAMETER = | 1.3351 |
| DISTANCE = | −8.3847 |

Figure 4:
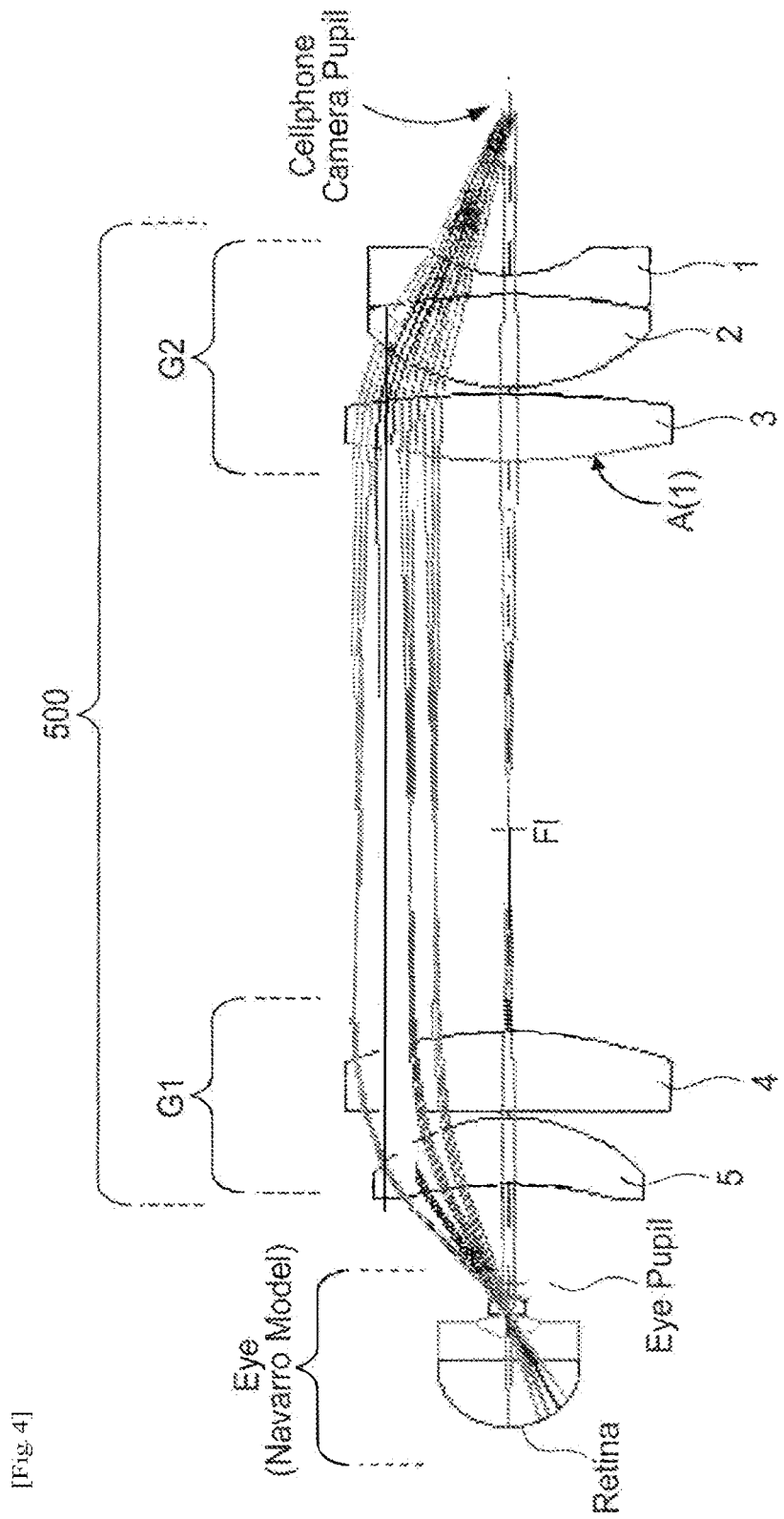
FIG. 4 illustrates a second embodiment of an optical train 500, representing an afocal relay system configured to the idea of the invention, and shown in combination with a Navarro model of a human eye.

The second embodiment 500 of the relay system of the invention structured as described in the above Tables 4, 5 and 6 is presented in FIG. 4 and has an effective focal length of 30.67 mm (modulus value), which results in formation of an image with a (paraxial) height of about 10.6 mm, and is corrected well for lateral color aberration(s). The embodiment of the lens system according to the idea of the invention contains only one, single aspheric surface A(1), which provides practical advantages (such as reduced costs). As shown in FIG. 4, the second embodiment contains a first lens group G1 and a second lens group G2. The first lens group G1 includes lens elements 4 and 5, and the second lens group G2 includes lens elements 1, 2 and 3. The Navarro model of the eye is also shown in combination with the relay system 500. The second lens group G2 includes a first meniscus lens element 1 having a negative dioptric power and in optical contact with the biconvex positive lens element 2, and the element 3 having a positive optical power and an aspheric surface A(1) and spatially separated from the combination of the elements 1 and 2. The second lens group G2 aggregately possesses positive optical power, overriding the negative optical power of the element 1. The first lens group G1 contains a positive lens element 4 and a second meniscus lens element 5 concave to the eye side, and has aggregately possesses positive optical power. The first lens group G1 is positioned close to the eye to be inspected, as shown by the Navarro model of the eye in FIG. 4.

Figure 5:
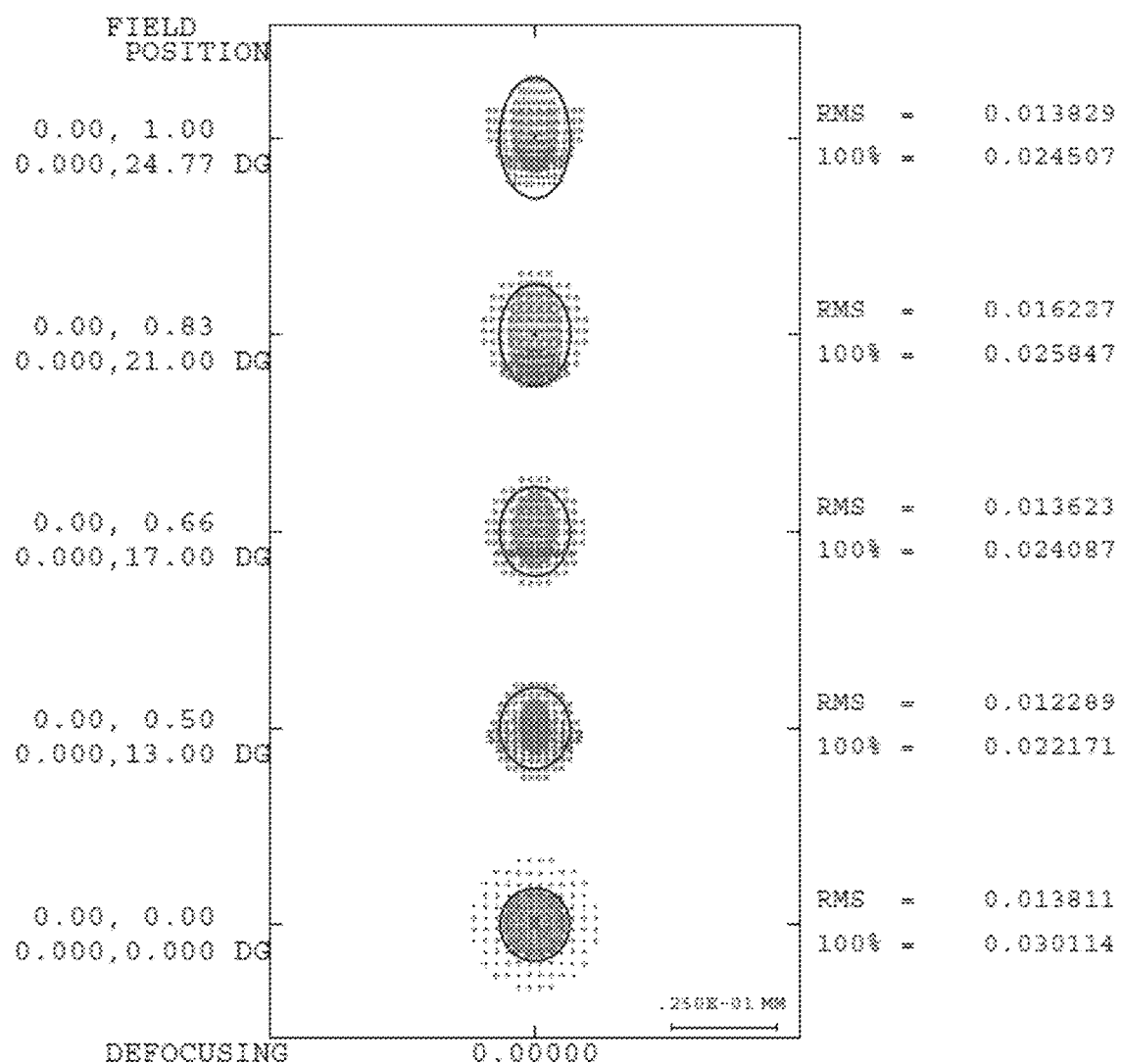
FIG. 5 shows spot diagrams of the second embodiment of FIG. 4 for different field heights.

FIG. 5 contains spot diagrams representing the effect of defocussing, while imaging an object with the second embodiment 500 of the invention, as a function of field position (expressed in degrees). The second embodiment is also shown to compensate for the aberrations of the (Navarro model) eye (at 2 mm eye pupil diameter, the healthy human eye is almost diffraction-limited) and provides close to diffraction-limited resolution across the entire 80 degree FOV. As convincingly evidenced by the spot diagrams falling within the Airy disk curve for each of the wavelengths, aberrations are substantially corrected over the whole visible spectrum, but are even smaller at the red end of the spectrum (where the backscattered light from the retina is about five times stronger than that in the blue, which is operationally preferred during the imaging of the retina). Such diffraction-limited performance across the visible spear urn critically and advantageously distinguishes the proposed invention from the related art. In practice, the proposed design of the optical system is such that diffraction-limited imaging of the retina is effectuated by balancing of optical aberrations typical for an average eye with those of the eye piece portion of the embodiment of the invention.

For each of the first embodiment and the second embodiment, values related to the focal lengths of the first lens group G1 and the second lens group G2 are shown below.

Embodiment 1

Focal length of Group 1 (eyepiece): f1=32.3
Focal length of Group 2 (objective): f2=34.4
Paraxial magnification: f2/f1=1.07

Embodiment 2

Focal length of Group 1 (eyepiece): f1=38.0
Focal length of Group 2 (objective): f2=53.0
Paraxial magnification: f2/f1=1.4

With respect to the relation between the wide angle retinal image size and the size of the image sensor there are two possible cases. In case 1, the magnification is chosen such that the 80 degree field of view entering the eye is imaged on to the camera to fill the diagonal of the screen (i.e., the size of the image sensor), as shown in FIG. 6A. This has the advantage that all of the camera pixels are used, but the disadvantage of losing some of the 80 degree field of view at the top, bottom and sides.

In case 2, the magnification is chosen such that the 80 degree field of view entering the eye is imaged on to the camera screen (i.e., the size of the image sensor) to fill the short dimension of the rectangular screen, as shown in FIG. 6B. This has the advantage that the whole 80 degree field of view is seen, but the disadvantage that not all of the camera pixels are used. This is the more common fundus camera situation but the two cases show that the invention can be applied to either situation by selecting the appropriate magnification close to 1.0, in the range 1.0 to 2.0.

A specific implementation of the invention can also be structured to take advantage of fundus imaging with a dual-lens (or, generally, a multiple-lens) cellphone camera. For example, if a cellphone has a second camera lens with a different focal length (for example, twice the focal length of the first lens of the cellphone), then—if and when the cellphone is shifted laterally or transversely with respect to the afocal relay of the invention to optically (axially) align the second lens with the afocal relay—the central angular portion of the retina (the one corresponding to the cellphone lens having the smaller FOV as compared to the FOV of another lens of the cellphone) can be imaged at a higher resolution. This is advantageous for more closely studying the foveal region and optic nerve, while retaining the capability to capture the whole retina by stitching to the short focal length camera. Alternatively, in this case, image stitching could be used with the longer focal length lens, to cover an 80 degree field of view or more at higher resolution.

The scope of the invention advantageously accommodates a situation in which a mobile device has multiple lenses (optical systems) disposed next to each other (as a 1D or 2D array of lenses, for example) and having different focal lengths (and, therefore, different FOVs). Here, the embodiment of FIG. 1 can be integrated with the back side of the mobile device through a contraption or positioner (driven mechanically or otherwise, for example, with the use of an electrical motor) configured to laterally reposition the embodiment in a plane perpendicular to the optical axes of such multiple lenses while maintaining the working (axial) distance between the embodiment and the plane in which the multiple lenses are disposed. When the embodiment is so translated to be co-axially disposed with a first lens of the cellphone camera, the optical conjugation is established between the EP of the eye and the EP of the first lens and the 1× imaging of the retina with the use of the telescope of the invention and the first first lens is advantageously enabled. When, at the next step of operation, the embodiment is translated to be co-axially disposed with a second lens of the cellphone camera, the optical conjugation is established between the EP of the eye and the EP of the second lens and the 1× imaging of the retina with the use of the telescope of the invention and the second lens is enabled. As a result of a multi-step (for example, N>1) repositioning, an N-position-zoom imaging system is practically implemented. It is appreciated that during so-configured imaging of the retina, the imaging of the retina with higher resolution is achieved (in the middle of the stitched image) when the cellphone lens having a smaller FOV is optically and mechanically cooperated with the embodiment of the afocal relay.

Furthermore, usually, the user will not have their spectacles on when pictures are taken, so a +/−10 Diopter adjustment can be provided by focusing the lenses closest to the eye—the eyepiece-based on the user's prescription. The camera's focusing system will adjust for fine focus.

According to the foregoing embodiments, a low-cost eye fundus camera having a simple and small-sized configuration is enabled. Further, compared to a conventional eye fundus camera using an attachment lens, it is clear that a superior eye fundus image can be obtained across a field of view that is approximately twice as broad and across a broad wavelength region. Further, when a multiple-lens cellphone camera is used, the degree of freedom of the field of view and the resolution performance increases.

Disclosed aspects, or portions of these aspects, may be combined in ways not listed above. Accordingly, the invention should not be viewed as being limited to the disclosed embodiments.

In the following, a third embodiment is explained with reference to FIG. 7.

As shown in FIG. 7, attachment 22 is a relay optical system that relays the pupil of subject eye 150 to the pupil position of the optical system of image capture portion 214 of cellphone 20, and is provided with first positive lens group G1 and second positive lens group G2. First positive lens group G1 and second positive lens group G2 have the same optical axis and substantially form an afocal system. The pupil of subject eye 150 is relayed to the pupil of the optical system of image capture portion 214 of cellphone 20 by the combination of the first positive lens group G1 and the second positive lens group G2.

The afocal relay of the invention, as an afocal attachment goes on the front of the cellphone camera lens. In this case, it serves to relay the cellphone camera pupil to the iris (pupil) of the patient.

When the afocal relay attachment 22 which is composed of the first positive lens group G1 and the second positive lens group G2 is disposed between subject eye 150 and the optical system disposed at the front side of image capture portion 214 of cellphone 20, as shown in FIG. 7), the configuration is such that the eye side focal position of the first positive lens group G1 is aligned with the pupil position of subject eye 150, and such that the focal position, at the side of cellphone 20, of second positive lens group G2 is aligned with the pupil position of the image capture optical system of cellphone 20. According to the configuration above the combination of the first positive lens group G1 and the second positive lens group G2 forms a conjugate relationship between the pupil of the subject eye and the pupil of the external optical system.

When the afocal attachment 22 including first positive lens group G1 and second positive lens group G2 is disposed, as shown in FIG. 7, at a position at which its optical axis is aliened with the optical axis of the image capture optical system of cellphone 20, image FI of the eye fundus of subject eye 150 is formed between the first positive lens group G1 and the second positive lens group G2.

The first positive lens group G1 includes, in the order from the side of the subject eye, positive meniscus lens 320, which has a concave surface facing the side of the subject eye, and positive lens 340, and the second positive lens group G2 includes, in the order from the side of the subject eye, positive lens 330 and meniscus lens 310, which has a convex surface facing the side of the subject eye.

Positive meniscus lens 320, which has a concave surface facing the side of the subject eye, is not limited to the configuration shown in FIG. 7, and may have the configuration shown in FIG. 2, being a compound lens including positive meniscus lens 6, which has a concave surface facing the side of the subject eye, and meniscus lens 5, which has a concave surface facing the side of the subject eye.

The meniscus lens 310 of the second positive lens group G2, which has a convex surface facing the side of the subject eye may, as shown in FIG. 7, be a compound lens of biconvex positive lens 310A and biconcave positive lens 310B cemented with each other. Further, it is possible, as appropriate, to adopt an aspherical surface as the shape of the lens surface, and in the second example, an aspherical surface is provided at the convex surface, at the side of the subject eye, of the biconvex lens of the second lens group G2.

When f1 is the focal length of the first lens group G1, f2 is the focal length of the second lens group G2, and D is the principal plane interval of both lens groups G1, G2, it is preferable that the following condition is substantially satisfied.

$$f1+f2=D$$

When, as described above, first positive lens group G1 and second positive lens group G2 substantially form an afocal system, it is preferable that the following condition is satisfied.

$$0.9 < f2/f1 < 2.2$$

In addition, in terms of practical use, the condition $1.0 \leq f2/f1 < 2.0$ is preferably satisfied.

It is preferable that the focal length f1 of the first lens group G1 and the focal length f2 of the second lens group G2 satisfy the following conditions.

$$30 \text{ mm} < f1 < 50 \text{ mm}$$

$$30 \text{ mm} < f2 < 60 \text{ mm}$$

The angle of view of the second lens group G2 at the side of the optical system of cellphone 20 includes, and preferably matches, the angle of view of the optical system of cellphone 20. The image of the image capture field of view (FOV) of the subject eye fundus corresponding to the angle of view of the first lens group G1 is transferred to the optical system of cellphone 20 via second lens group G2.

The 1× magnification of the relay optical system of attachment 22 of all the foregoing embodiments is the ideal for aberration correction; however, as mentioned above regarding the numerical conditions, a larger field of view than the cellphone camera is achieved by introducing a small amount of magnification, and the design is still able to achieve favorable aberration correction. A larger field of view is beneficial in that many pathologies of the retina can be seen within the 80 dg. field of view, and it is possible to switch to the cellphone telephoto lens camera to look in more detail at the central 40 dg. of the retina.

Further, attachment 22 is provided with a power source 380, a light source 362, which is supplied with power by the power source 380, and a beam splitter 372, which reflects light emitted from the light source 362 toward the side of second lens group G2 and passes light reflected from subject eye 150, via second lens group G2, through to cellphone 20.

In an image capture mode, which is described below, light emitted from the light source 362 is reflected, at the beam splitter 372, toward the side of second lens group G2 and arrives at the eye fundus of subject eye 150 via first lens group G1. Light that reached the eye fundus of subject eye 150 is reflected at the eye fundus, and the reflected light arrives at beam splitter 372 via the first lens group G1 and the second lens group G2, passes through the beam splitter 372, and arrives at the cellphone 20. The pupil of subject eye 150 is relayed to the pupil of the optical system of image capture portion 214 of the cellphone 20 by the first positive lens group G1 and the second positive lens group G2.

Next, a fourth embodiment is explained. Since the fourth embodiment shown in FIG. 8 has similar portions to the third embodiment, the same reference numerals are assigned to the similar portions and explanation thereof is omitted, while the different portions are explained.

As shown in FIG. 8, the afocal attachment 22 has, in addition to the first lens group G1 and the second lens group G2, a light source 362 and a power source 380 for the light source 362. Divergent light from light source 362 is collimated by a condenser lens 364. Then, the collomated light is incident at diffuser 366 and becomes divergent light, and irradiates ring diaphragm 368, which has a ring-shaped aperture. Light that passes through this ring-shaped aperture is reflected at beam splitter 372, and is guided to subject eye 150 through the second lens group G2 and the first lens group G1. Further, due to the action of the second lens group G2 and the first lens group G1, an image of the ring-shaped aperture of ring diaphragm 368 is formed on the pupil of the subject eye and irradiates the eye fundus of the subject eye.

Next, a fifth embodiment is explained. Since the fifth embodiment shown in FIG. 9 has similar portions to the third embodiment, the same reference numerals are assigned to the similar portions and explanation thereof is omitted, while the different portions are explained. As shown in FIG. 9, the afocal attachment 22 includes contact 382, which is connected to light source 362. Cellphone 20 includes a contact 20C, which is connected to the battery (not shown) of the cellphone 20. When the afocal attachment 22 is attached to cellphone 20, the contact 382 of the attachment 22 and the contact 20C of the cellphone 20 are connected. Since, as described above, the contact 382 is connected to the light source 362 and the contact 20C of the cellphone 20 is connected to the battery (not shown) of the cellphone 20, power from the battery (not shown) of the cellphone 20 is supplied to the light source 362 via the contact 20C and the contact 382.

In the fourth embodiment (refer to FIG. 8), it would be acceptable to omit the power source 380, and to provide the contact 382 at the attachment 22, and provide the contact 20C at the cellphone 20, such that when attachment 22 is attached to the cellphone 20, the contact 382 of the attachment 22 and the contact 20C of cellphone 20 are connected, and power from the battery (not shown) of the cellphone 20 is supplied to the light source 362 via the contact 20C and the contact 382.

While all of the examples described above use the beam splitter 372, it would be acceptable, in order to efficiently utilize the light from light source 362, to provide a polarizing beam splitter instead of the beam splitter 372, to dispose a polarizer between light source 362 and the polarizing beam splitter, and to provide an analyzer between the polarizing beam splitter and the cellphone 20. Further, it would be possible to insert a quarter wave plate between the second lens group G2 and the polarizing beam splitter, and adopt a configuration that supplies circularly polarized light to the subject eye.

Next, referring to FIG. 10, the electrical configuration of all of the above-described examples of cellphone 20 is explained. As shown in FIG. 10, the cellphone 20 is provided with computer 200. Computer 200 is provided with CPU 202, ROM 204, RAM 206, and input and output (I/O) port 208. CPU 202, ROM 204, RAM 206, and I/O port 208 are mutually connected via bus 210. I/O port 208 is connected to auxiliary storage device 212, image capture portion 214, speaker 216, display portion 218, communication portion 220, home button 222, image capture button 224, and autofocus mechanism 226.

Next, referring to FIG. 11, a method of use of attachment 22 and cellphone 20 is explained.

In Step 402, a user mounts attachment 22 at cellphone 20. When the power source switch of cellphone 20 is turned on, an eye fundus image capture application starts up in Step 404. In Step 406, the user holds their eye at the image capture position of image capture portion 214.

In Step 408, by turning on home button 222 of cellphone 20, CPU 202 initiates image capture mode. When image capture mode is initiated, image capture portion 214 captures an eye fundus image via attachment 22.

In Step 410, CPU 202 adjusts autofocus mechanism 226, automatically adjusts the focus, and when the focus is automatically adjusted, determines whether or not the eye fundus image capture range of image capture portion 214 is appropriate. Specifically, the position of the pupil of subject eye 150 is detected within the eye fundus image capture range of image capture portion 214 from the respective pixel values of the image data of the eye fundus image and from threshold values for distinguishing between a pupil portion and a peripheral portion. By determining whether or not the detected position of the pupil is within the image capture range, it is determined whether or not the image capture range is appropriate.

When it is determined that the eye fundus image capture range is inappropriate in Step 410, CPU 202 emits an audio instruction to change the hold position of cellphone 20 via speaker 216 in Step 412. For example, when the pupil position is at a higher position than the image capture range of image capture portion 214, "please raise the cellphone" is audio output via speaker 216. Instead of the audio output of "please raise the cellphone", or together with this audio output, "please raise the cellphone" may be displayed at display portion 218.

When it is determined that the position of the user's eye fundus is appropriately positioned in the image capture range of image capture portion 214, CPU 202 displays an image capture instruction at display portion 218 in Step 414. The user, having seen the image capture instruction displayed at display portion 218, turns on image capture button 224. The image capture instruction is not limited to being displayed at display portion 218, and an image capture instruction may be audio output via speaker 216 instead of, or in addition to, this display. When image capture button 224 is turned on, CPU 202 detects that image capture button 224 has been turned on in Step 416. When it has been detected that image capture button 224 has been turned on, the eye fundus image captured by image capture portion 214 is stored at auxiliary storage device 212 in Step 418, and, in Step 420, an image signal of the eye fundus image is transmitted to eye fundus image server 250 via communication portion 220.

Omitting the processing of Steps 414 and 416 when it has been determined that the position of the user's eye fundus is appropriately positioned within the image capture range of image capture portion 214, CPU 202 stores the eye fundus image captured by image capture portion 214 at auxiliary storage device 212 in Step 418, and transmits an image signal of the eye fundus image to eye fundus image server 250 via communication portion 220 in Step 420.

In all of the examples explained above, the cellphone 20 is provided with a single optical system (image capture lens system (camera lens)); however, the technique of the present disclosure is not limited thereto, and plural optical systems corresponding to plural angles of view may be provided. For example, in order to handle cases in which a peripheral portion surrounding the central portion of the eye fundus is to be captured in addition to the central portion, cellphone 20 may be provided with a first optical system for wide-angle use and a second optical system for standard use having a smaller angle of view than the wide angle. In a first mode that captures an image of the central portion and the peripheral portion of the eye fundus, an image of the central portion and the peripheral portion of the eye fundus would be formed at image capture portion 214 via the first optical system. In a second mode that only captures an image of the central portion, an image of only the central portion of the eye fundus would be formed at image capture portion 214 via the second optical system.

REFERENCE SYMBOL LIST

20 Cellphone
22 Attachment
G1 First lens group
G2 Second lens group
320 Meniscus lens
320A Meniscus lens
320B Meniscus lens
340 Positive lens
33 Positive lens
310 Meniscus lens
310A Biconvex lens
310B Biconcave lens
320 Positive meniscus lens
320A Positive meniscus lens
320B Meniscus lens

The invention claimed is:

1. A portable handheld relay optical system for forming an image of a fundus of a subject eye to be examined, said relay optical system being configured as an attachment optical system to be disposed between a portable handheld imaging device and the subject eye, the relay optical system, comprising:
 a first positive lens group G1 and a second positive lens group G2, wherein:
  the first positive lens group G1 and the second positive lens group G2 form an afocal system having an identical optical axis, and are configured to form a conjugate relationship between a pupil of the subject eye and a pupil of the imaging device when the relay optical system is inserted between the imaging device and the subject eye, and
  the first positive lens group G1 and the second positive lens group G2 substantially form an afocal relay system, and the following condition is satisfied:

$0.9 < f2/f1 > 2.2$, in which f1 is a focal length of the first positive lens group G1, and f2 is a focal length of the second positive lens group G2.

2. The relay optical system of claim 1, wherein:
when the relay optical system is disposed between the subject eye and the imaging device, the relay optical system is configured such that a focal position, at a side of the subject eye, of the first positive lens group G1 is aligned with a pupil position of the subject eye, and such that a focal position, at a side of the imaging device, of the second positive lens group G2 is aligned with a pupil position of the imaging device, and
an image of an eye fundus of the subject eye is formed between the first positive lens group G1 and the second positive lens group G2 and also formed in the imaging device.

3. The relay optical system of claim 2, wherein,
when D is a principal plane interval of both of the lens groups, the following condition is substantially satisfied:

$$f1+f2=D.$$

4. The relay optical system of claim 3, wherein:
the first positive lens group G1 includes, in order from a side of the subject eye, a positive meniscus lens having a concave surface facing the side of the subject eye, and a positive lens; and
the second positive lens group G2 includes, in order from the side of the subject eye, a positive lens and a meniscus lens having a convex surface facing the side of the subject eye.

5. The relay optical system of claim 4, wherein the positive meniscus lens of the first positive lens group G1 is formed as a composite positive meniscus lens composed of a positive meniscus lens element having a concave surface facing the side of the subject eye and a meniscus lens having a concave surface facing the side of the subject eye.

6. The relay optical system of claim 4, wherein a meniscus lens element of the second positive lens group G2 is formed as a composite meniscus lens composed of a biconvex lens and a biconcave lens.

7. The relay optical system of claim 1, wherein the following conditions are satisfied:

$$30 \text{ mm} < f1 < 50 \text{ mm}$$

$$30 \text{ mm} < f2 < 60 \text{ mm}.$$

8. The relay optical system of claim 1, wherein:
an angle of view of the second positive lens group G2 of the relay optical system at a side of the imaging device includes an angle of view of the imaging device; and
an image of an eye fundus of the subject eye corresponding to an angle of view of the first positive lens group G1 is transferred to the imaging device via the second positive lens group G2.

9. The relay optical system of claim 8, wherein the imaging device comprises an image capture lens of a portable camera.

* * * * *